(12) United States Patent
Bergveld et al.

(10) Patent No.: US 6,520,010 B1
(45) Date of Patent: Feb. 18, 2003

(54) SYSTEM AND METHODS FOR CHARACTERIZING A LIQUID

(75) Inventors: Piet Bergveld, Enschede (NL); Gerardus Rudolph Langereis, Enschede (NL); Wouter Olthuis, Enschede (NL)

(73) Assignee: JohnsonDiversey, Inc., Sturtevant, WI (US)

( * ) Notice: Subject to any disclaimer, the term of this patent is extended or adjusted under 35 U.S.C. 154(b) by 0 days.

(21) Appl. No.: 09/368,822

(22) Filed: Aug. 5, 1999

(30) Foreign Application Priority Data

Aug. 11, 1998 (EP) .............. 98202690
Mar. 17, 1999 (EP) .............. 99200818

(51) Int. Cl.⁷ .................................. G01F 1/68
(52) U.S. Cl. ................................... 73/204.26
(58) Field of Search ............. 73/204.24, 204.25, 73/204.26; 324/441, 678

(56) References Cited

U.S. PATENT DOCUMENTS

| 4,719,441 A | 1/1988 | Horn |
| 4,853,638 A | * 8/1989 | Endou et al. ............... 324/439 |
| 5,618,644 A | 4/1997 | Morita |
| 5,646,539 A | * 7/1997 | Codina et al. .............. 324/678 |
| 5,770,039 A | 6/1998 | Rigney et al. |

FOREIGN PATENT DOCUMENTS

| EP | 0 274 396 | 7/1988 |
| WO | 80/01513 | 7/1980 |
| WO | 91/18296 | 11/1991 |
| WO | 98/39648 | 9/1998 |

* cited by examiner

*Primary Examiner*—Hezron Williams
*Assistant Examiner*—Jewel V. Thompson
(74) *Attorney, Agent, or Firm*—Neil E. Hamilton; Warren R. Bovee; Renee J. Rymarz

(57) ABSTRACT

A system for characterizing a liquid comprises a sensor for providing an electrical output signal depending on a characteristic of the liquid, and a processing unit for processing the output signal of the sensor to obtain characterizing data of the liquid. The sensor is made as a single sensor/actuator device and can be connected in a plurality of manners to the processing unit. In at least some of these connecting manners the processing unit is adapted to actuate the sensor/actuator device and to process the output signal of the sensor/actuator device to obtain different characterizing data of the liquid.

7 Claims, 5 Drawing Sheets

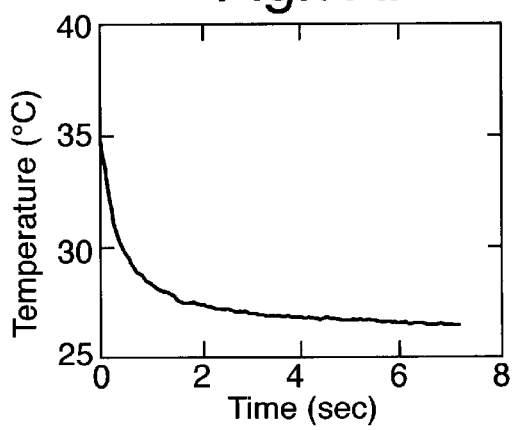
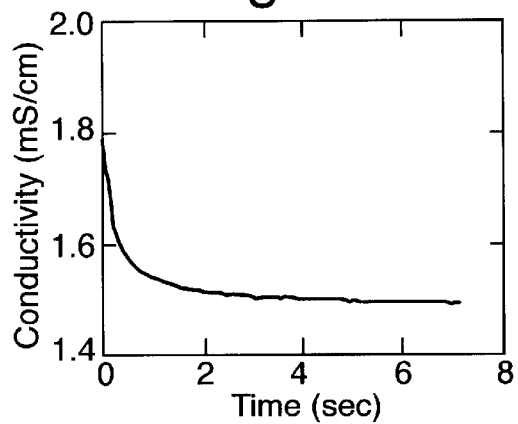
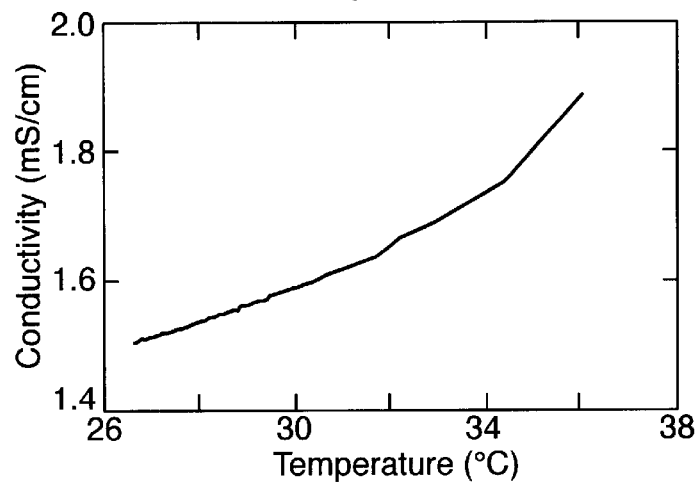
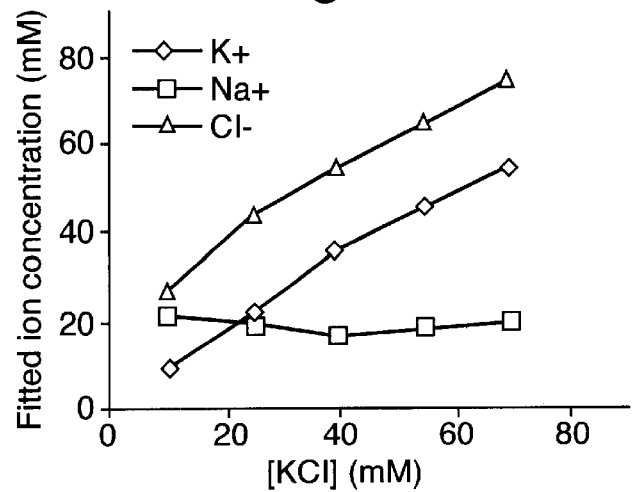

SYSTEM AND METHODS FOR CHARACTERIZING A LIQUID

FIELD OF THE INVENTION

The present invention relates to a system for characterizing a liquid, comprising a sensor for providing an electrical output signal depending on a characteristic of the liquid, and a processing unit for processing the output signal of the sensor to obtain characterizing data of the liquid, and to methods for characterizing a liquid.

BACKGROUND OF THE INVENTION

Known systems and methods for characterizing a liquid need the use of sophisticated devices which usually are designed for a single purpose, e.g. detecting specific ions in the solution. Such a system and method are for example disclosed in WO 98/39648. Devices to be used for determining characteristics of a solution, by immersion thereof in the liquid, are known from this document. Such devices are developed for specific purposes, e.g. measuring the temperature, or measuring the pH value of a solution. This implies that, for determining several characteristics of a solution, many different devices must be used in this known system. When, besides measuring characteristics of a liquid, some characteristics of a liquid have to be changed, e.g. if the temperature must be increased, until now separate devices were used for performing these actuating operations. This had the disadvantage that measures had to be taken so as to be able to immerse several devices in the liquid.

The present invention aims to provide an improved system and methods for characterizing a liquid of the above-mentioned type. Further, the invention has the object to provide a sensor with which different chemical and physical characteristics of a liquid can be measured and/or actuated.

DEFINITION OF THE INVENTION

According to the invention the system is characterized in that the sensor is made as a single sensor/actuator device, wherein means are provided for connecting the sensor/actuator device in a plurality of manners to the processing unit, wherein in at least a part of said plurality of connecting manners the processing unit is adapted to actuate the sensor/actuator device and to process the output signal of the sensor/actuator device to obtain different characterizing data of the liquid.

According to the invention bleach activity can be determined in a liquid, in particular a washing liquid, wherein a varying voltage is applied to the liquid through a working electrode and a counter electrode, wherein the current through the liquid is measured as a function of the varying voltage and the peak current value is determined, wherein the bleach activity is derived from the peak current value.

According to a further aspect of the invention ion concentrations in solution are determined by measuring the conductivity of said solution as a function of temperature, and deriving the ion concentrations from the measured values of conductivity and temperature.

DETAILED DESCRIPTION OF THE INVENTION

The invention will be further explained by reference to the drawings.

FIG. 1 schematically shows an embodiment of the system of the invention.

FIGS. 2A–2B schematically show structures of a sensor/actuator device used in the system of FIG. 1.

FIGS. 7A–7D shows some graphs to illustrate a second method of the invention.

Figure 1:
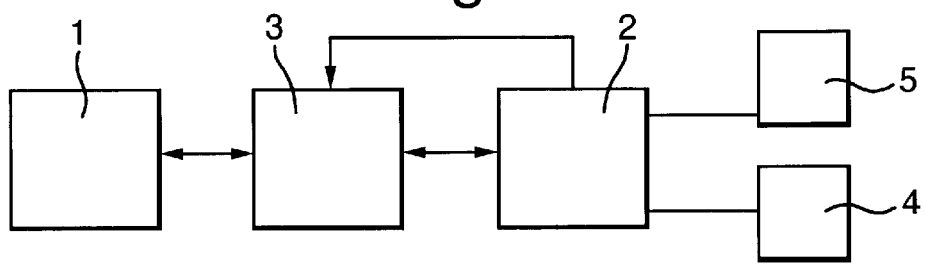

Referring to FIG. 1 there is shown a system for characterizing a liquid, which system comprises a sensor/actuator device 1 and a processing unit 2 for processing the electrical output signal of the sensor/actuator device 1. The device 1 is connected to the processing unit 2 through a switching circuit 3 which is controlled by the processing unit 2, as indicated by the single arrow connection in FIG. 1. The double arrow connections between components 1–3 indicate multiple lines for both sensing and actuating signals. Generally the processing unit 2 is part of a PC with a keyboard 4 and a monitor 5. The processing unit 2 is adapted to control the switching circuit 3 to connect the sensor/actuator device 1 in a plurality of manners to the processing unit 2 to operate the sensor/actuator device 1 in different manners. Thereby, different output signals will be provided by the sensor/actuator device 1 and by processing these different output signals, the processing unit 2 can obtain different characterizing data of the liquid as will be explained hereinafter.

Although in the embodiment shown in FIG. 1, the switching circuit 3 is controlled by the processing unit 2, it will be understood that the sensor/actuator device 1 can be connected in different manners to the processing unit 2 by manually changing the connection between the device 1 and the processing unit 2.

Figure 2A:
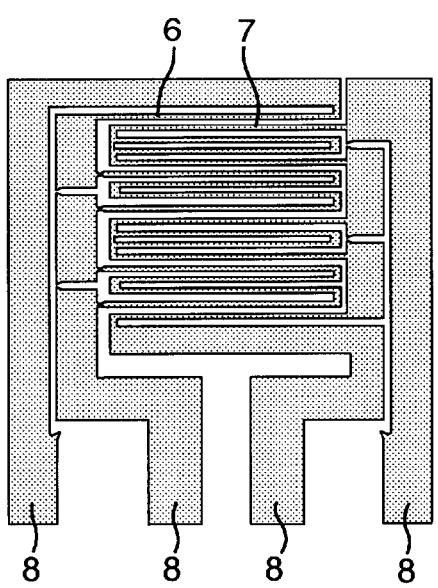
Figure 2B:
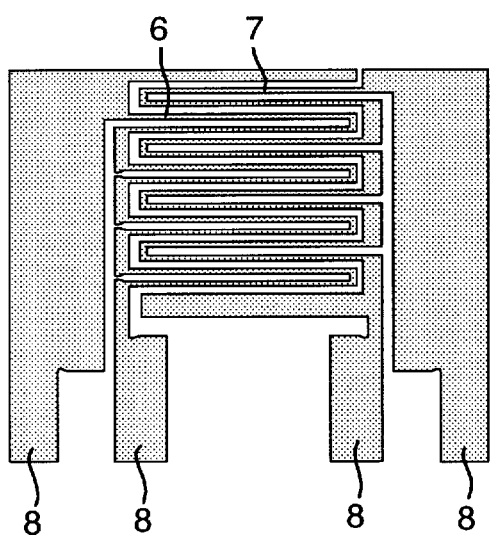

FIGS. 2A and 2B show two structures of the sensor/actuator device 1 of FIG. 1. In the embodiment of FIG. 2A the sensor/actuator device 1 comprises two resistive paths 6,7, each path having two terminal pads 8 for connecting the paths 6,7 to the switching circuit 3. As can be seen, both resistive paths 6,7 have a meandering, comb-like structure, wherein in FIG. 2A two teeth of the comb-like structure of resistive path 6 are placed between two teeth of the comb-like structure of the resistive path 7. In FIG. 2B each tooth of the comb-like structure of resistive path 6 is placed between two teeth of the comb-like structure of the resistive path 7. The intermediate gap between the resistive paths 6,7 is substantially constant.

Figure 3:
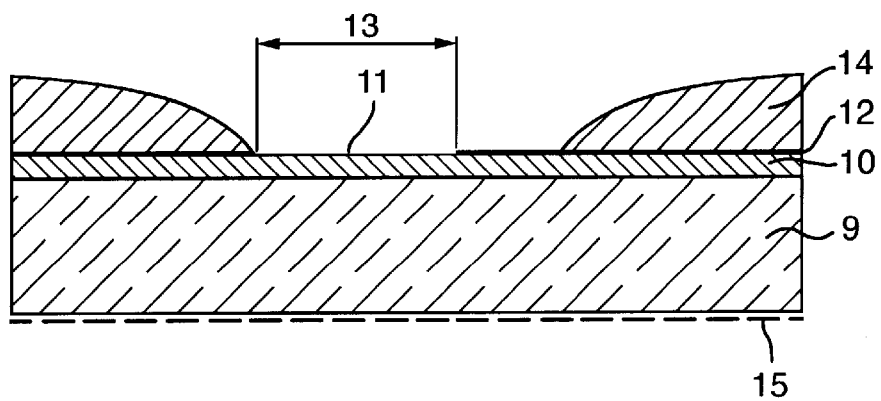
FIG. 3 shows a cross-section of the device of FIG. 2.

FIG. 3 shows a cross-section of an embodiment of the sensor/actuator device 1 realised on a glass substrate 9 using thin film technology. On the glass substrate 9 a silica film 10 is applied and on top of the silica film a platinum film 11 having a thickness of about 250 nm is deposited. The platinum film 11 is patterned by photolithography using wet chemical etching to obtain the pattern of either FIG. 2A or 2B. The platinum film 11 is surrounded by a polyimide insulation window 12 covering the substrate 9 except for the active area 13 showing the meandering structure and the terminal pads 8. Finally, a protecting layer 14 of Hysol® has been applied. It is noted that for adhesion purposes a 20 nm tantalum layer can be applied on the glass substrate and on top of the platinum film. The tantalum layer can be patterned using reactive ion etching.

In the embodiment of FIG. 2A, the size of the meander area is 1 mm$^2$, the width of the paths is 47 $\mu$m, the width of the gap is 5 μm and the resistance of the paths 6,7 is 92 Ω. In the embodiment of FIG. 2B, the size of the meander area is 1 mm$^2$, the width of the paths is 45 μm, the width of the gap is 15 μm and the resistance of the paths 6,7 is 78 Ω.

It is noted that the sensor/actuator device can be made in another manner, for example as a printed circuit board. Such an embodiment results in a relatively cheap production of the device. The copper layer of the PCB can be gold plated where necessary. Other substrates are generally possible, such as e.g. flexible or non-flexible plastic materials.

The system with the sensor/actuator device 1 shown in FIG. 1 shows the advantage that a number of different characterizing data of a liquid to be examined can be obtained using the same sensor/actuator device 1, i.e. the device 1 is a multi-sensing device and moreover can be used as an actuator. Due to the single sensor/actuator device, the system is adapted to apply a stimulus to the liquid examined while measuring. Thus, a functional integration of a sensor and actuator is obtained. The use of a single sensor/actuator device 1 results in a reduction of noise in some stimulus-response measurements. For, the measurement before and after a stimulus is carried out using the same sensor and therefore, the same offset (noise) will be observed which can be eliminated by subtracting the sensor output signals.

As a first example, the system can be used to measure water movement or flow by heating the local environment through resistive path 6, for example, while monitoring the temperature through resistive path 7. A faster movement of the water will result into lowering of the observed local temperature. When used in a washing machine, this decrease in the observed resistance of path 7 can be used as an indication for the mechanical washing effectiveness.

As a further example, the system of FIG. 1 can be used to apply an amperometric bleach activity detection method. Amperometry is found to be an attractive tool for monitoring bleach activity since it can be used to measure the bleaching components in the way they are intended to do their work during washing, i.e. reductively or oxidatively decomposing a target species. It does not matter what component is included in the detergent for the bleaching operation, as one just wants to know the effectiveness of stain removal by redox mechanisms. In order to use the sensor/actuator device for amperometric bleach detection, the backside of the substrate 9, i.e. the surface opposite of the resistive paths 6,7, is provided with a counter electrode 15 having a size which is much lager than the size of the active area 13 of the device 1. The counter electrode 15 is schematically indicated in FIG. 3 by a dashed line. The complete active area 13 is used as a working electrode by interconnecting the terminals 8 of the paths 6,7. The processing unit 2 provides a varying voltage to the liquid through the working and counter electrodes and the current through the working electrode is measured by the processing unit.

Figure 4A:
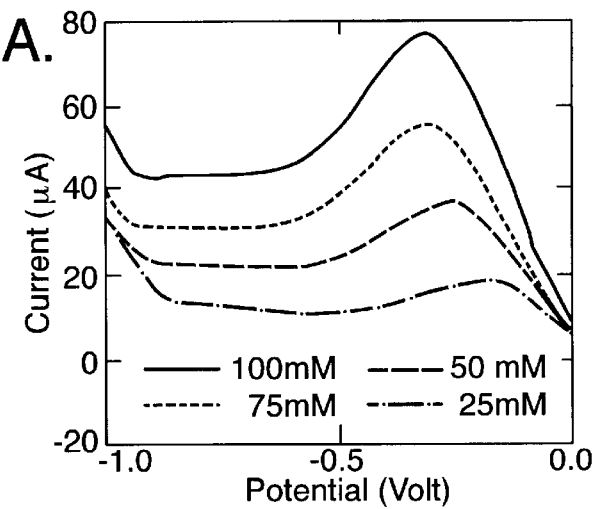
FIGS. 4A–4D show some graphs to explain a first method of the invention.
Figure 4B:
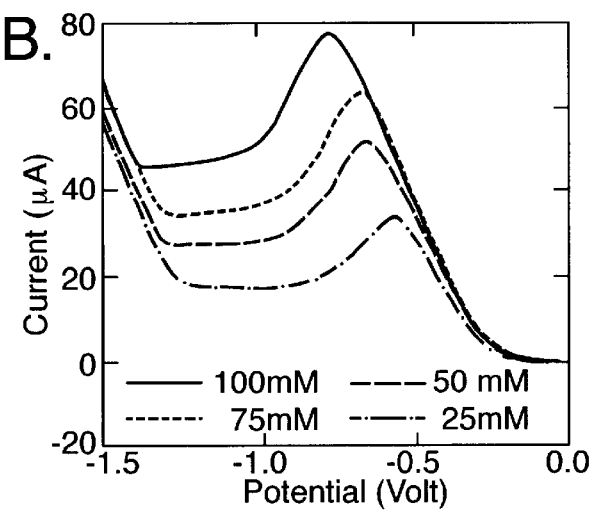
Figure 4C:
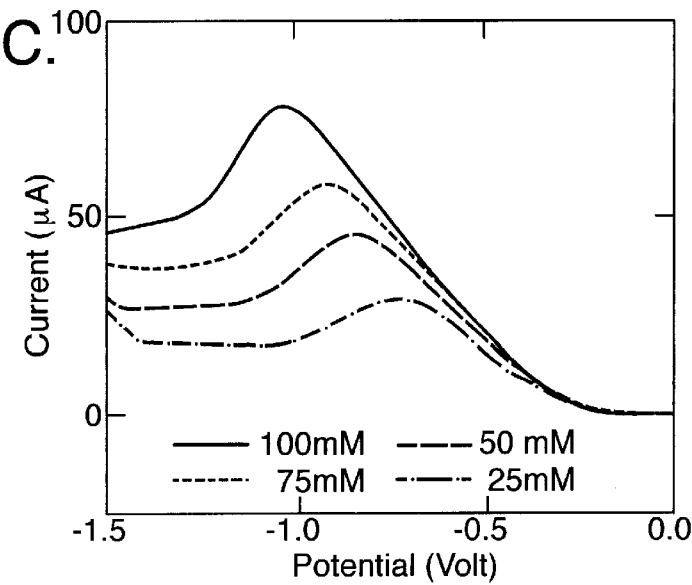
Figure 4D:
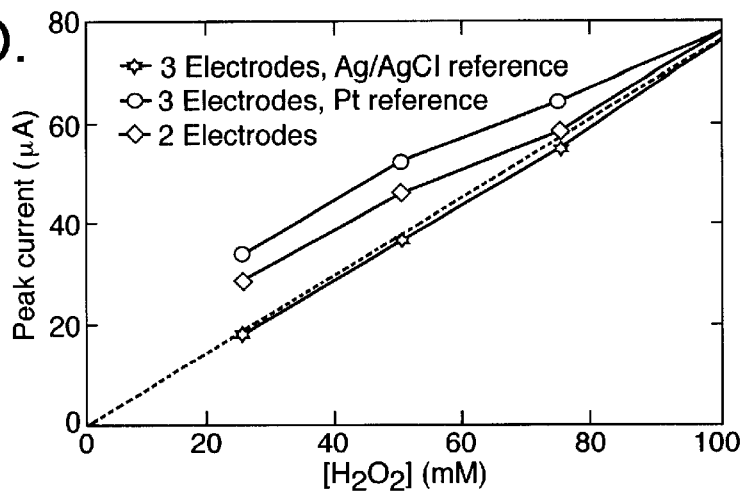

Experiments show that the height of the peak current through the working electrode is a measure for the bleach activity of the liquid, such as for example washing water. The voltage is preferably varied from approximately 0 down to –1,0 V. FIGS. 4A and 4B show potential sweep voltammograms in various concentrations $H_2O_2$ obtained in experiments using an Ag/AgCl reference electrode (A) and Pt reference electrode (B). FIG. 4C shows corresponding sweep voltammograms in a two electrode system, i.e. working and counter electrodes only. From these potential sweep voltammograms the peak values of the current measured are plotted in FIG. 4D showing that the height of the peak current is an indication for the hydrogen peroxide concentration. As the process responsible for the peak current represents the oxidative capability of the electrolyte under test, the principle represented by FIGS. 4A–D not only applies to hydrogen peroxide but to any bleaching material.

Figure 5A:
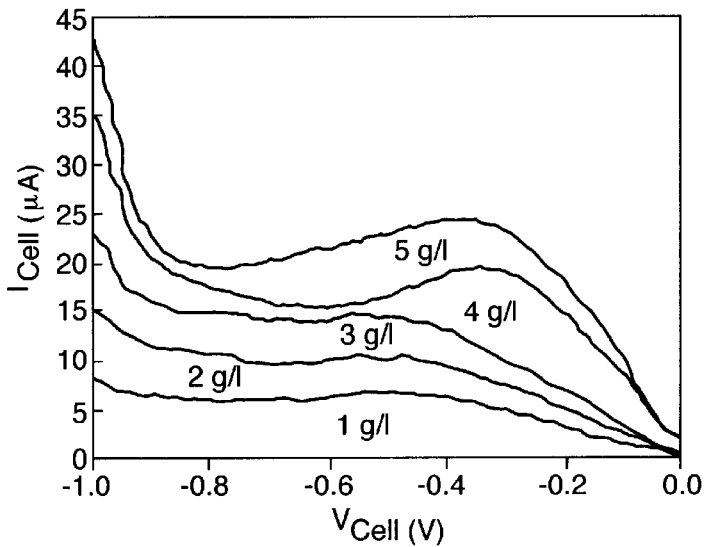
FIGS. 5A–5B show graphs to explain an example of an embodiment of the invention to determine bleach activity.
Figure 5B:
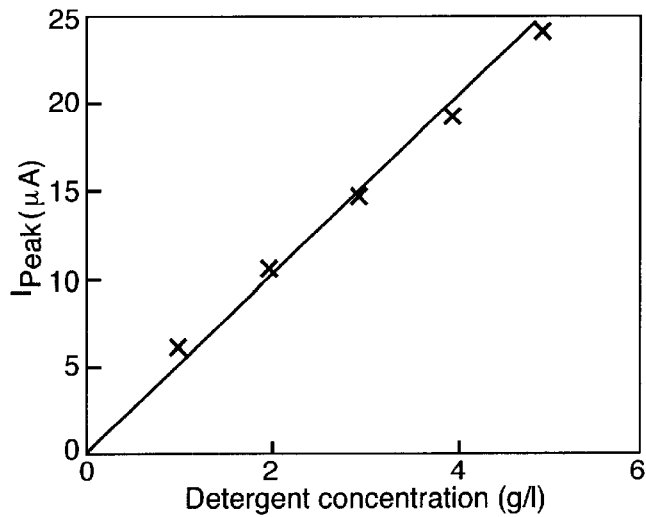

FIGS. 5A and 5B show an example with the two electrode set-up, in which a washing liquid was made by dissolving 1, 2, 3, 4 or 5 g detergent per liter tap water. The detergent used is Dobbelman Compact®, a synthetic powder with bleach. Before each measurement the solution is heated up to 40° C. since this is also the case during washing. The size of the counter electrode 15 is 1×0, 5 cm$^2$. The sweep voltammograms are shown in FIG. 5A and the peak currents measured are plotted in FIG. 5B showing that the peak current value is proportional to the applied detergent concentration. As the size of the counter electrode 15 is much larger than the size of the working electrode, a relatively low current density is obtained at the counter electrode, so that any possible reactions at the counter electrode will not be present significantly in the voltammogram.

The experiments and example show that with the sensor/actuator device 1 with counter electrode 15 bleach activity can be measured with sufficient selectivity by using a specific voltage sweep from approximately 0 down to –1,0 V. The type of bleaching system is not of interest and by using the sufficiently negative potential sweep, an electrical current is obtained, the peak value of which is proportional to the bleach effectiveness. The position of the peak with respect in the sweep voltage range was surprisingly found to be irrelevant to the detection method.

Figure 6A:
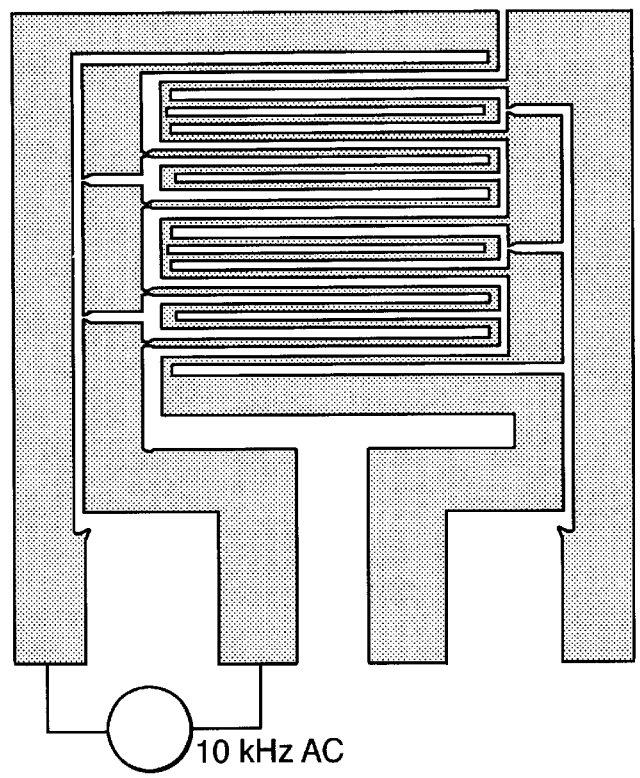
FIGS. 6A–6B show the use of the sensor/actuator device as connected in the system of FIG. 1 to apply the method illustrated in FIG. 7.
Figure 6B:
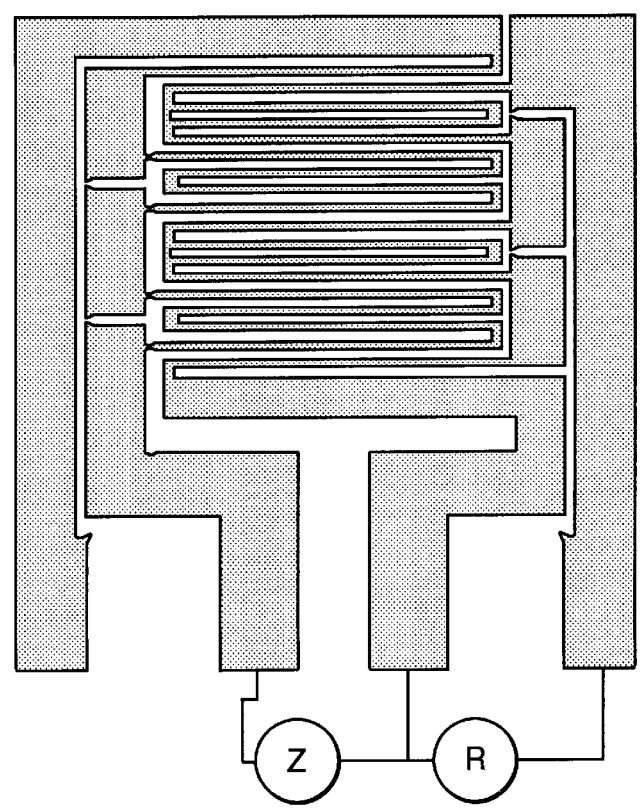

A further application of the system shown in FIG. 1 is illustrated in FIG. 6. FIG. 6A shows the sensor/actuator device of FIG. 2A, wherein resistive path 6 is used to heat the local environment of a liquid to be examined. A 20 V top to top voltage of 10 kHz is connected to the terminal pads 8 of path 6. This heating power is maintained for a few seconds. Directly after switching off the heating power, the resistance of the path 7 and the impedance at 1 MHz between the two paths 6,7 are measured simultaneously for about seven seconds. The resistance of path 7 is a measure for the local temperature, and can be calibrated before and after the measurement. The impedance between the paths 6,7 at 1 MHz provides a measure for the conductivity of the liquid.

The measured temperature and conductivity while cooling down as measured by the processing unit 2, are shown in FIGS. 7A and 7B, respectively. The two graphs of FIGS. 7A and 7B can be combined to form one single graph showing the conductivity of the liquid as a function of temperature.

This graph is shown in FIG. 7C. The solution measured in this example consisted of 100 mM KCl in demi water with a quality of 0,5 μS/cm.

From the conductivity as a function of temperature, the processing unit 2 is adapted to determine separate ion concentrations. The separate ion concentrations can be calculated using the characteristic temperature responses of these ion types. The calculation of the separate ion concentrations from the liquid conductivity is possible as the total electric conductivity Λ of an electrolyte in terms of the separate ion contributions is given by $$\Lambda = \Sigma \lambda_i C_i Z_i$$

with $\lambda_i$ the limiting molar conductivity, $C_i$ the concentration and $Z_i$ the charge of ion i. The limiting molar conductivity of $\lambda_i$ is dependent on temperature and can be approximated by a polynomial fit:

$$\lambda_i(T) = \lambda_i^o \sum_{n=o}^{N} \alpha_{i,n}(T-T_0)^n$$

Since the coefficients $\alpha_i$, n are unique for ion i, the total conductivity $\Lambda$ is a unique linear combination of the limiting molar conductivities $\lambda_i$ (T) with the ion concentrations as coefficient.

In FIG. 7D fitted ion concentrations in five solutions with 25 mM NaCl and several KCl concentrations are shown. The separate concentrations of the three ions were determined from the measured conductivity versus temperature curves.

It will be understood that the system described shows the advantage that selectivity in sensing is not achieved by providing a specific sensor structure or material used, but by controlling the sensor/actuator device and mathematical evaluation of the signals obtained. In the amperometric method described, the use of a potential sweep from 0 down to −1,0 V provides the selectivity and by measuring the current peak bleach activity can be determined. As the bleach activity is measured in the way bleach is supposed to work, the method is universal, and not dependent on the typical substance accounting for the bleach operation. The method described measures the bleach activity directly by observing the oxidising strength of the bleaching material.

As a second method, ion concentration measurement is possible by a conductivity measurement which as such is not selective for specific ions. However by measuring the conductivity as a function of temperature, data is obtained providing ion specific information. This information can be extracted from the conductivity/temperature function by assuming a set of ions with known temperature dependencies of their specifical conductivities and estimating the best ion concentrations that fit with the measured conductivity-temperature relation.

Although in the above-described embodiments the methods are carried out using the system of the invention, it is noted that these methods can be applied using different measuring systems, i.e. for example different sensors and actuators.

According to the invention, the ion concentration method can be applied in a washing process by defining a local volume in which the composition of the washing liquid is a simplification of the washing water. Such a local volume for the sensor/actuator device can be provided by means of suitable filtration membranes.

The system described can advantageously be used for measuring variables and washing parameters to control the washing process. First, in the tap water used for washing, the electrolyte conductivity can be measured by means of the sensor/actuator device 1. Conductivity of tap water shows a large correlation to water hardness. From the conductivity of the tap water, the hardness can be estimated and this estimation can be used by the processing unit 2 to control the amount of added builder.

After the laundry is soaked by the tap water, the conductivity of the liquid can be measured again. As soluble parts of the soil present on the laundry will be dissolved in the water, the new conductivity measured will be different from the conductivity of the tap water and this difference will be an indication of the soil particles dissolved in the water. This indication can be used to control the amount of detergent added. During the washing process, the bleach activity can be monitored and the decay of the bleaching component can be shown on monitor 5. Based on the speed of this decay, the processing unit 2 or an operator can decide to add more bleach or to stop the bleaching cycle. A similar monitoring of the washing operation can be based on the electrolyte conductivity.

Further, as described above, the device 1 can be used as a flow sensor to determine whether or not the tub of the washing machine is rotating. Further the water temperature can be measured.

When, at the end of the main wash, the water and laundry in the tub do not consume added builder and bleach anymore, the washing process can be stopped. Thereafter a series of rinsing cycles is started as usual. During rinsing the possible excesses of detergent and residues of washing are removed. The sensor/actuator device is switched to monitor the electrolyte conductivity and based on this conductivity measurement it can be determined when the residues are removed and the rinsing can then be stopped.

The invention is not restricted to the embodiments as described, which can be varied in a number of ways within the scope of the appending claims.

What is claimed is:

1. System for characterizing a liquid, comprising a sensor for providing an electrical output signal depending on a characteristic of the liquid, and a processing unit for processing the output signal of the sensor to obtain characterizing data of the liquid, the processing unit including a user input and a user output, characterized in that the sensor is made as a single sensor/actuator device, wherein means are provided for connecting the sensor/actuator device in a plurality of manners to the processing unit, wherein in at least a part of said plurality of connecting manners, the processing unit is constructed and arranged to actuate the sensor/actuator device and to process the output signal of the sensor/actuator device to obtain different characterizing data of the liquid.

2. System according to claim 1, wherein the processing unit is adapted to actuate the liquid while measuring a parameter of the liquid.

3. Sensor/actuator device to be used in a system according to claim 1, wherein the sensor/actuator device comprises two resistive paths and two connecting terminal for each path, wherein said paths each have a meandering, comb structure and wherein teeth of each comb structure are placed between the teeth of an other, to form an intermediate gap between said resistive paths of substantially constant width.

4. Sensor/actuator device according to claim 3, wherein the sensor/actuator device comprises a planar electrode having a surface a size of which is substantially larger than the size of the two resistive paths.

5. Sensor/actuator device according to claim 3, wherein one tooth of the comb structure of a first resistive path is placed between two teeth of the comb structure of a second resistive path.

6. Sensor/actuator device according to claim 3, wherein two teeth of the comb structure of a first resistive path are placed between two teeth of the comb structure of a second resistive path.

7. System according to claim 3, wherein said meandering paths consist of planar electrodes on a substrate of an electrically insulating material.

* * * * *